United States Patent [19]

McFaul et al.

[11] Patent Number: 4,947,416
[45] Date of Patent: Aug. 7, 1990

[54] SCANNING EQUALIZATION RADIOGRAPHY WITH STATIONARY EQUALIZATION DETECTOR

[75] Inventors: James A. McFaul, Waukesha; Gary S. Keyes, Hartland; David L. McDaniel, Dousman, all of Wis.

[73] Assignee: General Electric Company, Milwaukee, Wis.

[21] Appl. No.: 260,769

[22] Filed: Oct. 21, 1988

[51] Int. Cl.$^5$ ............................................. G21K 5/10
[52] U.S. Cl. ................................. 378/146; 250/385.1; 378/150; 378/151
[58] Field of Search ..................... 378/146, 150, 151; 250/385.1

[56] References Cited

U.S. PATENT DOCUMENTS

| | | | |
|---|---|---|---|
| 4,310,766 | 1/1982 | Finkenzeller et al. | 250/509 |
| 4,366,574 | 12/1982 | Hill | 378/99 |
| 4,404,591 | 9/1983 | Bonar | 358/111 |
| 4,433,427 | 2/1984 | Barnea | 378/146 |
| 4,504,962 | 3/1985 | Moore | 378/19 |
| 4,675,893 | 6/1987 | Duinker | 378/146 |
| 4,677,652 | 6/1987 | Duinker et al. | 378/151 |
| 4,715,056 | 12/1987 | Vlasbloem et al. | 378/152 |

Primary Examiner—Craig E. Church
Attorney, Agent, or Firm—Douglas E. Stoner; James O. Skarsten

[57] ABSTRACT

A scanning type radiographic imaging system is disclosed which employs novel means to produce comparable radiation intensity in the object regions being radiographed. Such result is achieved with variable radiation attenuating elements having their attenuation controlled during this scanning process with novel feedback control means. The feedback control is produced with a stationary detection unit having circuit means which generates the electrical control signals.

8 Claims, 3 Drawing Sheets

SCANNING EQUALIZATION RADIOGRAPHY WITH STATIONARY EQUALIZATION DETECTOR

BACKGROUND OF THE INVENTION

The present invention relates in general to scanning radiography with beam equalization and more specifically to a stationary equalization detector including electronic scanning or including variable detector channel size.

Scanning or slit radiography has been known for a number of years as a technique for reducing x-ray scatter in the radiographic image. In the known scanning radiographic systems, a moving x-ray beam is produced by a movable x-ray source to which is attached single or multiple collimators or slits thus producing a moving x-ray beam. Alternatively, the x-ray source may be stationary while the collimator is movable to create the moving x-ray beam. Known scanning x-ray systems include a movable pencil beam which scans the object in a two-dimensional raster scan and a fan beam approach which scans the object in a single direction. The radiographic image produced by either of these two methods is being used for medical purposes.

It frequently occurs that the body to be imaged includes both material that has high x-ray attenuation and material that has low x-ray attenuation. In order to avoid an x-ray image of such body in which some parts of the image are overexposed while other parts are underexposed, dynamic equalization of localized x-ray exposure has been employed. As a result, the dynamic range of the image is compressed to be within the dynamic range of the film or other detector which forms the image.

Scanning equalization is usually achieved with a separate equalization detector (i.e., separate from the image detector) which often scans along with the x-ray beam behind the body being imaged. The output of the equalization detector controls the x-ray exposure to each portion of the body, usually by varying an amount of attenuation introduced between the x-ray source and each respective body portion. Alternatively, the exposure time or the x-ray intensity can be varied, as in the scanning pencil beam approach. Thus, the image detector receives an exposure which is controlled to be within its dynamic range.

An example of the prior art using a scanned fan beam is U.S. Pat. No. 4,715,056 issued to Vlasbloem et al. on Dec. 22, 1987. This radiographic system employs a slit diaphragm which moves relative to an x-ray tube. An x-ray detector or a scintillator for producing an image moves along with the scanned fan beam to receive x-rays after they have passed through the body being imaged. Light from the scintillator is projected onto a film which records the image. An additional light detector for controlling equalization scans along with the image detector (e.g., scintillator) to sense the image intensity for a plurality of image sections along the slot of the fan beam. Signals from the equalization detector control corresponding variable attenuation sections in the slit diaphragm.

According to the Vlasbloem et al. patent, the light detection device used for equalization could consist of a series of photosensitive elements on the housing of the scintillator or a series of lenses and photomultiplier tubes. In one alternative embodiment, a single CCD matrix may be used for acquiring a digitized image and for controlling equalization. In another alternative embodiment, a large area, stationary scintillation screen is used in conjunction with an equalization detector comprising vertically arranged, strip-like photoconductors disposed at the front of the screen.

The foregoing prior-art arrangements have serious drawbacks which have limited the usefulness, efficiency, and cost effectiveness of scanning equalization radiography systems in the clinical environment. Movable equalization detectors require a mechanical linkage between the moving x-ray tube/diaphragm combination and the detector. To reduce sensitivity to scattered radiation, the prior art required a scanning slot located between the body and the imaging detector, the scanning slot being mechanically-coupled or servo-coupled to the slit mechanism controlling the fan beam. Such mechanical linkage is susceptible to breakage and interferes with patient and film cassette positioning. The use of a CCD matrix is expensive and is not readily adaptable to systems using film. The embodiment with a large scintillating screen and strip-like photoconductors is susceptible to signal degradation from scatter transverse to the fan beam unless the strips are located close to the screen. All of the prior-art arrangements have equalization detector channels of fixed size and so are unable to properly control systems with variable source-to-image distances (SIDs) which cause the image area covered by each variable attenuation section of the slit diaphragm to vary.

Accordingly, it is a principal object of the present invention to provide scanning equalization without the above-mentioned drawbacks.

It is another object of the invention to provide a scanning equalization method and apparatus employing a stationary detector which avoids signal contamination by scatter.

It is a further object of the invention to provide a scanning equalization method and apparatus employing a stationary detector adaptable to variable source-to-image distance.

It is yet another object to provide means to convert existing radiography systems to perform scanning equalization with minimum modification to the existing system and to avoid introducing moving mechanical components at the x-ray receptor.

SUMMARY OF THE INVENTION

These and other objects of the invention are achieved with an x-ray detector for controlling scanning x-ray equalization comprising a first chamber wall, a second chamber wall spaced from the first chamber wall to define an ionization region therebetween, and a gas contained within said ionization region. The first chamber wall includes a plurality of parallel electrodes contacting the gas and extending in a first direction which define a plurality of active zones in the detector and which are each connected to a source of electric potential for collecting ions produced by x-rays penetrating the ionization region. The second chamber wall includes at least one electrode contacting the gas and extending in a second direction perpendicular to the first direction which is connected to a source of electric potential to create a potential difference across the ionization region in at least one of the active zones.

In one preferred embodiment, each of the electrodes on the first chamber wall is connected to a separate amplifier. The amplifier outputs are controllably grouped together to form active zones of variable size. Thus, the size and number of channels in the equalization detector can be varied in response to a change in source-to-image distance (SID) which also changes the size of the image area controlled by each variable attenuation section in the slit diaphragm.

In another preferred embodiment, the second chamber wall includes a second plurality of parallel electrodes contacting the gas and extending in the second direction. The second plurality of electrodes are each connected to an electric potential in a controlled manner to perform electronic scanning in the first direction along with the fan beam. This decreases sensitivity to scattered radiation since the only region of the detector sensitive to x-rays is then the area directly in line with the scanning x-ray beam.

In operation, the equalization detector is located between the object being radiographed and the photographic film for recording the x-ray image. The first plurality of electrodes act as collecting electrodes and are oriented parallel to the direction of travel of the x-ray fan beam. The collector electrode network generates x-ray intensity signals which are used to control the individual attenuation elements of the slit diaphragm. The signals from the electrodes corresponding to each attenuation element are summed in a series of signal adders. The electrode signals are coupled to the adders through a switch network which is controlled in accordance with image-to-source distance.

BRIEF DESCRIPTION OF THE DRAWINGS

The novel features of the invention are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE PREFERRED EMBODIMENTS

Figure 1:
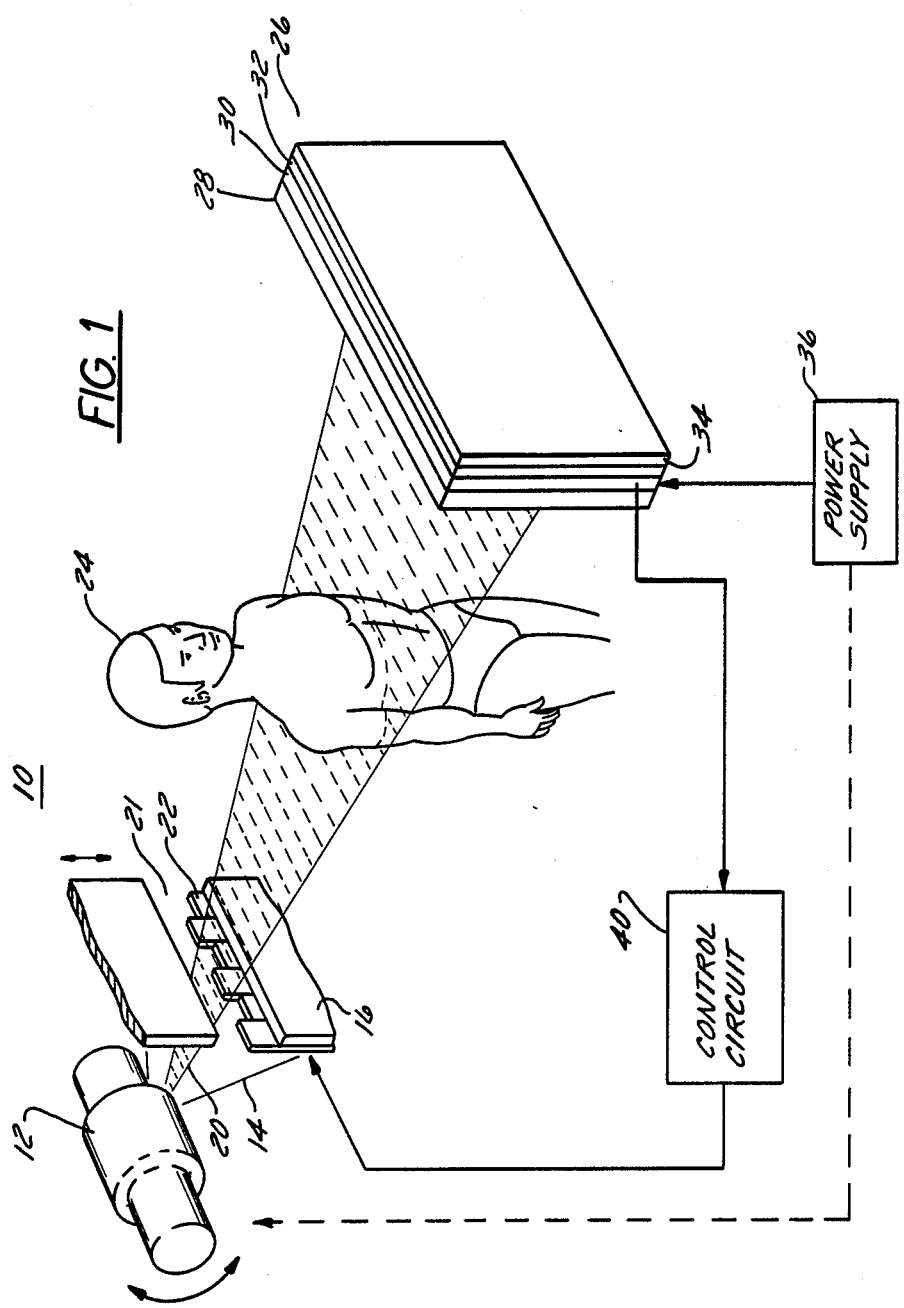
FIG. 1 is a schematic representation partially in block diagram form of a scanning equalization radiography system.

Referring to the drawings, FIG. 1 depicts partially in block diagram form a typical scanning radiographic imaging system in accordance with the present invention. Such apparatus 10 employs a conventional rotatable x-ray tube 12 to provide a horizontal x-ray beam 14 of suitable size corresponding in area to the overall object being scanned for exposure of the selected region, such as for a medical patient 24. The emerging x-ray fan beam is further modulated with a collimator 16 to provide a moving x-ray fan beam 20 being employed to irradiate the medical patient. Such moving x-ray fan beam results from motion of the rotating x-ray tube source and a slot opening or slit 21 provided in the collimator 16 relative to the stationary patient 24 and a detector unit. The thin fan beam 20 instantaneously cuts a slice through patient 24. The direction within the slice which is perpendicular to the direction of the propagation of x-rays is referred to herein as the slice direction. In a pencil beam system, each raster line of a scan corresponds to a separate slice, while in a fan beam system, the slice advances continuously.

A plurality of movable mechanical attenuating elements 22 modulate the slot opening with each of the attenuating elements having its movement controlled during scanning in a manner so as to substantially equalize the intensity of x-ray radiation being applied with respect to different body portions of the medical patient. While such moving controlled x-ray fan beam is depicted in the present drawings as proceeding in a generally vertical direction, it will be evident to one skilled in the art that an opposite or different travel direction can be utilized with suitable repositioning of the presently described cooperating structural components.

The x-ray radiation in the moving fan beam passes through the medical patient 24 for subsequent processing in a stationary detection unit 26 which is constructed as a flat planar housing member. Detection unit 26 is shown to comprise, for example, a Bucky grid 28, an equalization detector 30, a phosphor screen 32, and image recording means 34 which typically comprises photographic film or a film holder or cassette.

An electrical power supply 36 is connected to equalization detector 30. Power supply 36 receives information concerning the position of x-ray tube 12 and/or collimator 16, as shown by a dashed line, so that power supply 36 can selectively energize equalization detector 30 in accordance with the current position of x-ray fan beam 14, as will be described later in more detail.

Electrical output signals from equalization detector 30 are provided to a control circuit 40 which generates control signals applied to variable attenuating elements 22 in a manner to equalize the signals received from equalization detector 30. Control circuit 40 is comprised of a feedback control circuit of a type having a construction which is known in the art.

Bucky grid 28, scintillating phosphor screen 32, and x-ray film or film cassette 34 are well known in the art and further description thereof will be omitted.

Equalization detector 30 preferably comprises an ion detection chamber having a pair of juxtaposed chamber walls and a gas contained therebetween. Electrodes on each chamber wall contact the gas and are energized to provide an electrical potential across the gas resulting in an ionization region. X-rays passing through the chamber ionize the gas in proportion to the intensity of the x-rays. The electrodes collect the ions resulting in an electrode current proportional to the x-ray intensity. Such an ion chamber can be placed between patient 24 and x-ray film holder 34 because x-ray beam 20 is substantially unattenuated by the ion chamber. The ability to place equalization detector 30 in front of the film holder makes the invention easily adaptable to retrofitting existing non-equalizing, film-based radiographic units for scanning equalization.

Figure 2:
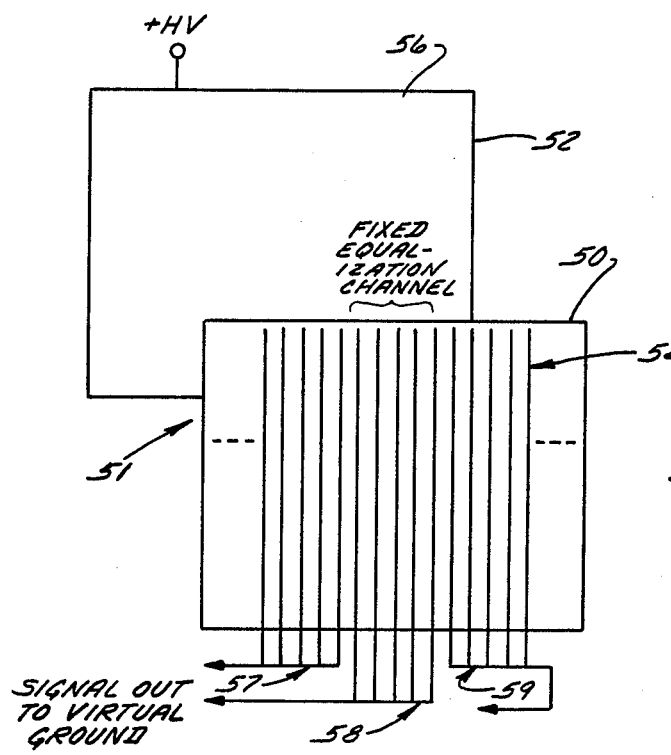
FIG. 2 is an elevation view depicting an equalization detector according to the present invention.

FIG. 2 is an elevation view of one preferred embodiment of an equalization detector including a first ion chamber wall 50 and a second chamber wall 52. A gas at 51 is any gas capable of being ionized by x-rays such as air. An electrode grid network on wall 50 is comprised of a plurality of conductive runs 54 disposed on wall 50 in contact with gas 51 and extending in a direction parallel to the direction of travel of the scanning of the x-ray fan beam. A sheet electrode 56 is disposed on wall 52 in contact with gas 51 and is of substantially equal extent as the grid network of conductive runs 54.

Sheet electrode 56 is coupled to a source of high voltage +HV. Conductive runs 54 are grouped into a plurality of active zones 57, 58, and 59 by directly interconnecting groups of conductive runs corresponding to the equalization channels of the attenuating elements. Three active zones are shown to simplify the drawings, however, there generally will be many more than three zones. The conductive runs in each active zone are coupled to ground or virtual ground, such as would be provided at the input of a signal amplifier (not shown). Thus, a potential difference across the ionization region of each active zone is provided such that the conductive runs collect ions in proportion to the x-rays passing through each zone. The total current in all of the conductive runs of the respective active zone provides an output signal for input to the control circuit of the attenuating elements.

Figure 3:
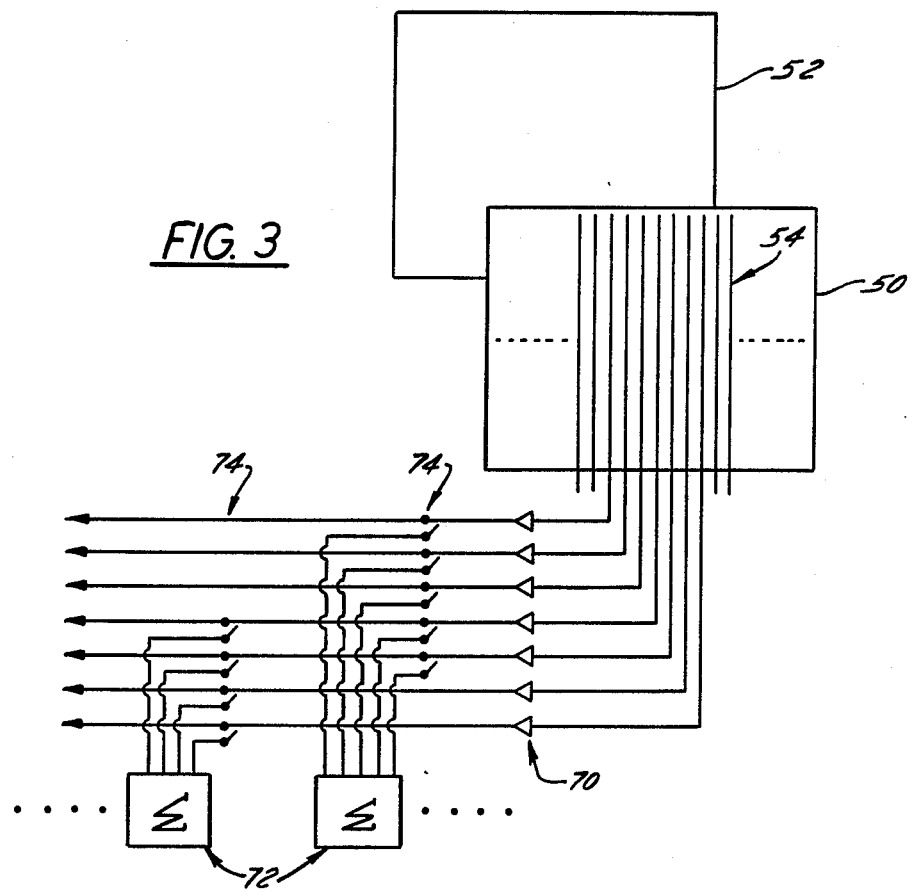
FIG. 3 is a part elevation view of the equalization detector and a part schematic, block diagram of control circuitry of the invention.

The size of each active zone can be fixed, as illustrated in FIG. 2, or, as in the embodiment of FIG. 3, can be variable, in which case the ionization current signal from each individual conductive run is collected separately. The signals are then selectively added together in a manner allowing the detector to change the effective size and position of the active zones. Such a feature would enable the invention to be used on imaging systems with a variable source-to-image distance (SID). As shown in FIG. 3, the individual output signals of electrode runs 54 are each fed to a virtual-ground input of a respective amplifier 70 which provides the amplified signal for each collecting electrode to one of a plurality of electronic summing elements 72 as determined by electronically activated switches 74. From the summing elements, the summed signals are processed by control circuit 40 as described above. The settings of switches 74 determine the grouping of conductive runs into active groups, each of which measures the exposure modulated by a single attenuating element 22. Each conductive run is connected by switches 74 to a single summing element 72 which is determined by the particular source-to-image distance being employed. Electrical power is preferably supplied to amplifiers 70, summing elements 72, and switches 74 by power supply 36 (FIG. 1).

Figure 4:
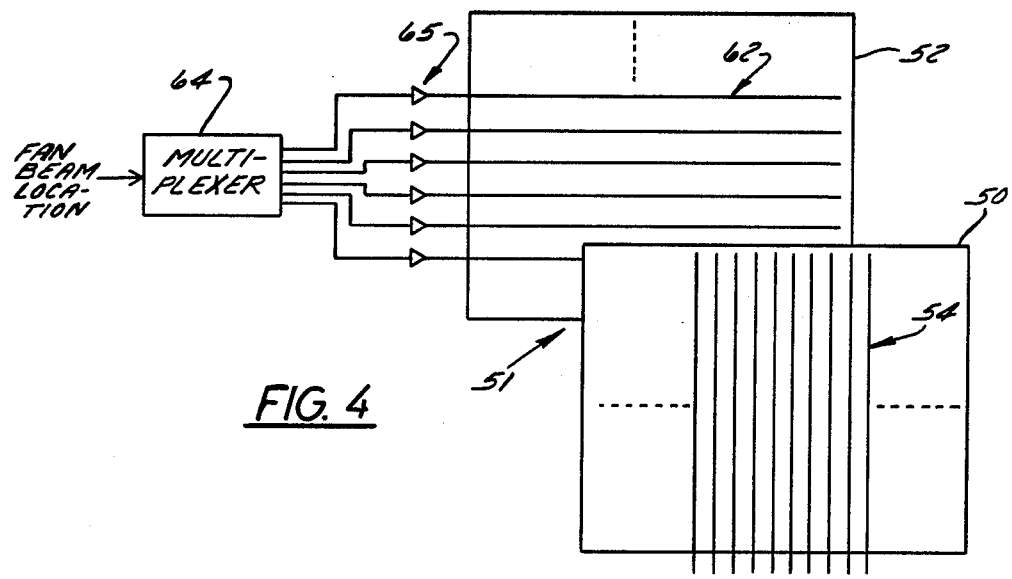
FIG. 4 is an elevation view of a further embodiment of the equalization detector of the invention.

Another embodiment of equalization detector 30 is shown in FIG. 4 wherein first chamber wall 50 and the interconnection of runs 54 may be as shown in either FIG. 2 or FIG. 3. However, in this embodiment, second chamber wall 52 has an electrode grid network of conductive runs 62 disposed thereon in contact with gas 51 and extending in a direction perpendicular to the direction of travel of the fan beam. Each conductive run 62 is coupled to a multiplexer 64 through a respective high voltage driver 65.

The purpose of this configuration is to provide electronic scanning of the equalization detector in order to reduce susceptibility to scattered radiation. In operation, only a portion of conductive runs 62 are energized at a time during scanning so as to limit the area of the detector which is sensitive to ionization by x-rays passing therethrough. Multiplexer 64 is electronically controlled by apparatus (not shown) which also controls the position of the scanning fan beam in such a manner that only the conductive runs 62 which are currently directly in line with the fan beam are energized.

Figure 5:
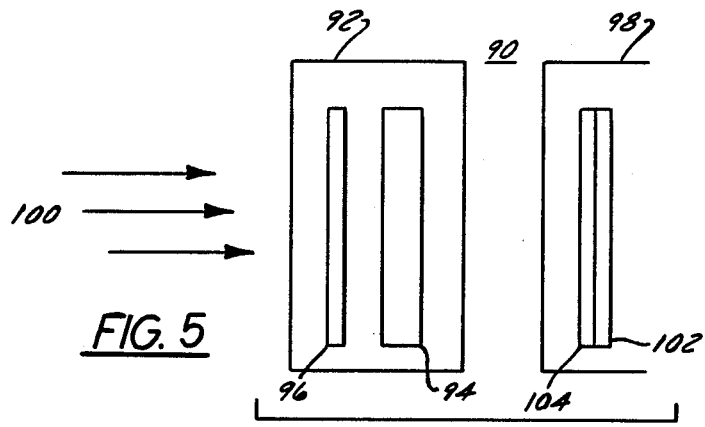
FIG. 5 is a cross-sectional view of an add-on detection arrangement of the present invention.

In FIG. 5 there is depicted a side view of an illustrative stationary detection unit employing a retrofit ion chamber detection means. Such an add-on unit is easily adaptable to conventional manual and automatic film changers. For example, the add-on unit could be constructed to fit as a replacement for the automatic exposure control ionization chamber present in many existing manual and automatic film changers in non-scanning-equalization systems. The depicted stationary unit 90 employs a housing member 92 containing an equalization detector 94 according to this invention together with Bucky grid means 96. As such, the stationary detection unit is suitable for modification of existing scanning radiographic apparatus in order to provide equalization for recorded film images. The depicted housing member can thereby be joined to or physically supported by a conventional photographic film cassette 98 generally employed in such existing radiographic equipment of this type without causing substantial attenuation of the moving x-ray beam 100 before recording the radiographic image. The conventional film cassette herein illustrated employs a film member 102 operatively associated with a conventional phosphor screen member 104. Contrast equalization of the recorded film image again proceeds with the X radiation emerging from the radiographed object being simultaneously detected by the particular ion chamber detection means employed.

It will be apparent from the foregoing description that broadly useful means have been provided to improve equalization detection in scanning radiography. It will be apparent from said foregoing description, however, that various modifications in the specific embodiments above described can be made without departing from the spirit and scope of the present invention. For example, it is contemplated that a moving x-ray beam having a pencil configuration can be employed. Moreover, still other physical configurations of the presently improved scanning radiographic system than above specifically disclosed are possible so long as the essential dynamic relationships above disclosed are preserved between cooperating x-ray scanning means and the stationary detection unit.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. X-ray exposure equalization apparatus in a system including a source of an X-ray beam; means for selectively moving the X-ray beam in a first direction to scan the beam through a plurality of slices extending through an object; and means receiving the scanned x-ray beam to record an image of the object, wherein the apparatus comprises:

means for selectively attenuating each of a plurality of discrete portions of said x-ray beam;

means for detecting the radiation level of each of the discrete beam portions, said radiation level detecting means comprising means responsive to x-ray radiation and supported between the object and the image recording means so that movement of the scanned x-ray beam relative to the radiation level detecting means and the image recording means is the same;

said radiation level detecting means comprising a first chamber wall, a second chamber wall spaced apart from said first chamber wall to define an ionization region therebetween, and a gas contained within said ionization region, said first chamber wall including a plurality of parallel first electrodes contacting said gas and extending in a second direction perpendicular to said first direction, said second chamber wall including at least one second electrode contacting said gas and extending in said first direction;

means coupled to said plurality of parallel first electrodes and to said at least one second electrode for creating a potential difference across said ionization region; and control means for maintaining the radiation level of each beam portion within a specified range comprising a plurality of signal summing means, each for generating an output signal representing the sum of the input signals thereto, each respective output signal from each respective signal summing means being coupled to control a corresponding one of said attenuating means, and switch means for coupling each of a selected number of said first electrodes to each of said signal summing means to controllably group said first electrodes into a plurality of active zones corresponding to said beam portions, each coupled first electrode providing an input signal, and for varying said selected number of coupled first electrodes to vary said active zones in corresponding relationship with variations in the distance between said beam source and said image recording means.

2. The apparatus of claim 1 wherein:
the radiation level detecting means comprises means adjustable to limit the area of said radiation level detecting means which is sensitive to x-ray radiation at a specified time to an area which is traversed by the scanned x-ray beam at the specified time.

3. The apparatus of claim 1 wherein said radiation level detecting means comprises a stationary radiation detector mounted between the object and a stationary image recording means.

4. The apparatus of claim 1 wherein:
a plurality of parallel second electrodes are supported by said second chamber wall to contact said gas and to extend in said first direction; and
means are provided for energizing only a portion of said second electrodes at a specified time to limit the area of said radiation level detecting means which is sensitive to ionization by x-rays passing therethrough at the specified time to an area corresponding to the energized second electrodes.

5. The apparatus of claim 1 wherein said attenuating means comprises a slit diaphragm having a plurality of controllable variable attenuation elements, each element corresponding to one of said beam portions.

6. The apparatus of claim 1 wherein said second chamber wall includes a single second electrode comprising a sheet electrode extending in said first and second directions adjacent to the entire ionization region.

7. The apparatus of claim 1 wherein said image recording means comprises a photographic film.

8. The apparatus of claim 7 wherein said image detector further comprises a phosphor screen.

* * * * *